US008077946B2

(12) United States Patent
Oosawa

(10) Patent No.: US 8,077,946 B2
(45) Date of Patent: Dec. 13, 2011

(54) APPARATUS AND PROGRAM FOR ASSISTING REPORT GENERATION

(75) Inventor: Akira Oosawa, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 911 days.

(21) Appl. No.: 12/101,656

(22) Filed: Apr. 11, 2008

(65) Prior Publication Data

US 2008/0253631 A1     Oct. 16, 2008

(30) Foreign Application Priority Data

Apr. 11, 2007  (JP) ................. 2007-103842

(51) Int. Cl.
G06K 9/00 (2006.01)
G06K 9/34 (2006.01)
G06K 9/32 (2006.01)
(52) U.S. Cl. ......... 382/128; 382/131; 382/173; 382/294
(58) Field of Classification Search .................. 382/128, 382/131
See application file for complete search history.

(56) References Cited

U.S. PATENT DOCUMENTS

| 7,130,457 | B2 * | 10/2006 | Kaufman et al. | 382/128 |
| 7,158,692 | B2 * | 1/2007 | Chalana et al. | 382/294 |
| 7,467,119 | B2 * | 12/2008 | Saidi et al. | 706/21 |
| 2007/0019849 | A1 * | 1/2007 | Kaufman et al. | 382/128 |

FOREIGN PATENT DOCUMENTS

| JP | 9-187444 A | 7/1997 |
| JP | 2005-160502 A | 6/2005 |
| JP | 2006-155002 A | 6/2006 |

OTHER PUBLICATIONS

William F. Sensakovic, et al, "Automated Matching of Temporally Sequential CT Sections", Med Phys., 2004, pp. 3417-3424, vol. 31, No. 12 (Dec. 2004).
Wormanns D. et al., "Volumetric Measurements of Pulmonary Nodules At Multi-Row Detector CT: in Vivo Repoducibility", Eur Radiol, 2004, vol. 14, No. 1 (Abstract)/Epub Nov. 13, 2003.
T. Hayashi, et al., "Development of the Procedure for Automatic Extracting Interlobar Fissures and Its Performance Evaluation", Technical Report of IEICE, 2003, pp. 39-44, MI2003-53(Oct. 2003).
Thomas M. Lehmann, et al, "Content-Based Image Retrieval in Medical Applications: A Novel Multi-Step Approach", Procs SPIE, 2000 vol. 3972.

* cited by examiner

Primary Examiner — Brian Werner
Assistant Examiner — Utpal Shah
(74) Attorney, Agent, or Firm — Sughrue Mion, PLLC

(57) ABSTRACT

A burden in generating a follow-up observation report is reduced. The size of an abnormal shadow present on a current medical image obtained by imaging a subject is measured, and the size of an abnormal shadow present on a previous medical image, which has been obtained by imaging the same subject, at a position corresponding to the position the abnormal shadow on the current medical image is measured. A character string describing a change in the size is generated from the measured sizes of the two abnormal shadows, and a file of a report text, containing the character string, about a case shown in the previous and current medical images is outputted.

5 Claims, 9 Drawing Sheets

FIG.5A

|  | SLICE 1 | SLICE 2 | SLICE 3 | SLICE 4 | SLICE 5 | SLICE 6 | ... |
|---|---|---|---|---|---|---|---|
| HEAD REGION | -0.3 | -0.2 | -0.5 | -0.7 | -0.9 | -0.7 |  |
| HEAD-NECK REGION | 2.0 | 1.2 | 0.1 | -0.5 | -0.8 | -0.5 |  |
| NECK REGION | -0.3 | -0.1 | 1.2 | 0.6 | 1.1 | 0.5 |  |
| CHEST REGION | -0.5 | -0.3 | -0.1 | 0.7 | 0.6 | 1.3 |  |
| .... |  |  |  |  |  |  |  |

FIG.5B

|  | SLICE 1 | SLICE 2 | SLICE 3 | SLICE 4 | SLICE 5 | SLICE 6 | ... |
|---|---|---|---|---|---|---|---|
| HEAD REGION | 2.3 | 1.4 | 1.7 | 2.1 | 2.0 | 2.0 |  |
| HEAD-NECK REGION | 0 | 0 | 1.1 | 1.9 | 1.9 | 1.8 |  |
| NECK REGION | 2.3 | 1.3 | 0 | 0.1 | 0 | 0.8 |  |
| CHEST REGION | 2.5 | 1.5 | 1.3 | 0 | 0.5 | 0 |  |
| .... |  |  |  |  |  |  |  |

FIG.5C

|  | SLICE 1 | SLICE 2 | SLICE 3 | SLICE 4 | SLICE 5 | SLICE 6 | ... |
|---|---|---|---|---|---|---|---|
| HEAD REGION | 2.3 | 1.4 | 1.7 | 2.1 | 2 | 2 |  |
| HEAD-NECK REGION | 0 | 0 | 0 | 1.1 | 1.9 | 1.9 |  |
| NECK REGION | 0 | 1.3 | 0 | 0.1 | 1.1 | 2.7 |  |
| CHEST REGION | 2.3 | 1.5 | 2.3 | 0 | 0.6 | 1.1 |  |
| .... |  |  |  |  |  |  |  |

FIG.8
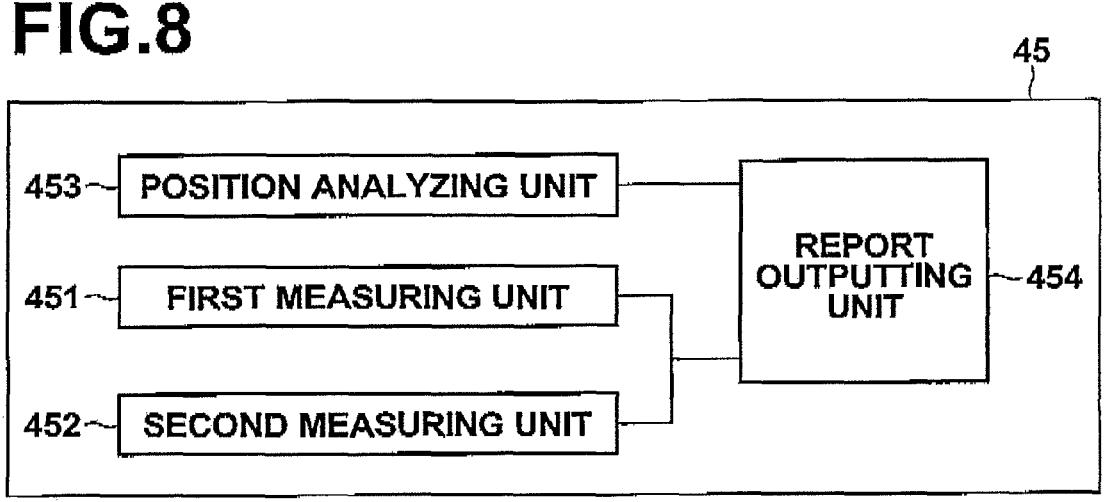
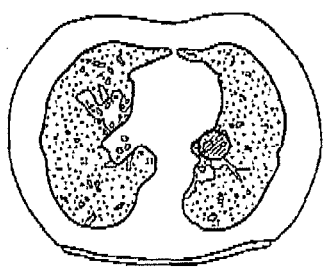
FIG.9B
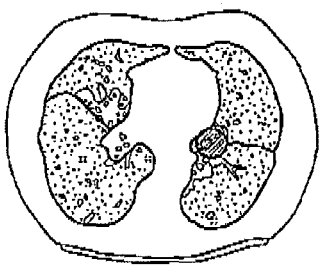
FIG.9C
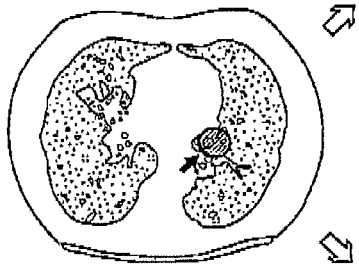
FIG.9A
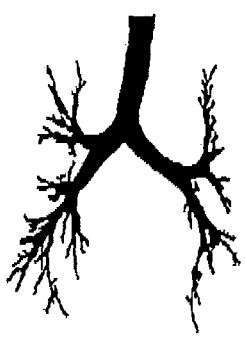
FIG.9D
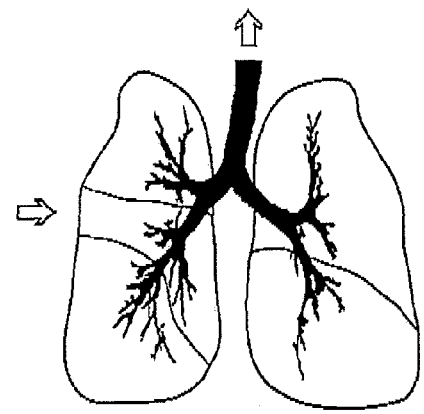
FIG.9E ☐POSITION: LEFT LUNG, SUPERIOR LOBE, S2
☐SIZE: AREA = 55.2 mm², AXIS MAJOR = 9.5 mm,
  AXIS MINOR = 6.8 mm
☐DIAGNOSIS: NC (NO CHANGE)

REMARKS

⟨NODULE⟩ IS ⟨FOUND⟩ AT ⟨RIGHT LUNG⟩
⟨ SUPERIOR LOBE⟩ ⟨S2⟩

DIAGNOSIS
⟨NO CHANGE⟩ IN THE SIZE OF THE ⟨NODULE⟩

APPARATUS AND PROGRAM FOR ASSISTING REPORT GENERATION

BACKGROUND OF THE INVENTION

1. Field of the Invention

The present invention relates to an apparatus and a program for assisting generation of a report about a medical image.

2. Description of the Related Art

In imaging diagnosis, a medical staff, such as a diagnostician, observes medical images to carry out diagnosis and writes remarks and reports. In order to streamline and speed up operations in medical institutions, digitalization of such reports using computers to replace reports written on sheets of paper is under way. Further, systems have been proposed, which store digitalized reports in a shared server which is accessible from more than one terminals, so that more than one doctors can share the reports and utilize them.

Texts in such reports are often inputted freely, however, writing a report with observing a displayed medical image takes time and trouble. Therefore, a method for reducing burden in generating such reports has been provided (see, for example, Japanese Unexamined Patent Publication No. 2005-160502). In this method, example sentences describing medical images are associated and stored with information attached to the medical images, such as the type of an imaging apparatus, the region, the time and date of testing and the patient identification information. When a report about a certain medical image is generated, suitable example sentences are automatically selected from these example sentences based on inputted attached information, and characteristics of a lesion contained in the medical image are applied to the selected example sentences. Further, generated example sentences and reports can be edited, and previous reports about the patient can be utilized.

Another problem lies in that, since character strings used to describe a certain case varies depending on the person who inputs the texts (operator), it is difficult to determine which character strings the case is typically represented with. This will result in nonuniform quality of the image interpretation reports. In addition, since the number of specialists who can interpret medical images, such as radiographic images, is not large, it is necessary to improve quality and efficiency of image interpretation in such a field. In order to generate the image interpretation reports with a certain level of uniformity without depending on the diagnostician who interprets the image, or improve quality and efficiency of image interpretation in a field where the number of the specialists is small, it is desired to positively utilize previous cases and previous image interpretation results. Therefore, a system for assisting report generation has been provided (see, for example, Japanese Unexamined Patent Publication No. 2006-155002). In this system, stored report files are structuralized using tag information for associating attributes of items contained in each report with contents of the report so as to reduce influences of specific character strings used to describe the case, and image interpretation reports to be referenced are searched based on the tag information so that not only reports containing the same character string(s) but also those having matching item attributes and contents are searched out, to allow positive utilization of the previous cases and previous image interpretation results.

In imaging diagnosis carried out in follow-up observations, it is necessary to accurately measure the size of a lesion, such as a suspected cancer or a cancer undergoing a chemical treatment, in current and previous images to determine whether the size of the lesion has increased, decreased or not changed.

At present, the diagnosticians manually measure the size of the lesion in the current and previous images, and calculate a change in the size to write a follow-up observation report. However, measuring the size of the lesion is a delicate work, and is a large burden for the diagnosticians. The diagnosticians typically measure the size of the lesion in the previous image again to ensure accurate diagnosis without trusting a previous result of measurement even if the previous measurement was conducted by themselves.

With the above-described techniques, previous reports can be used to reduce burden in generating a report, however, the size of a lesion, which is important in the follow-up observation, has to be manually measured before inputted, and the burden of the measuring work cannot be reduced.

SUMMARY OF THE INVENTION

Therefore, the present invention is directed to providing an apparatus and a program for assisting report generation, which can reduce burden in generating a report in follow-up observation.

The apparatus for assisting report generation of the invention includes: a first measuring unit to measure a size of an abnormal shadow present on one of a previous medical image and a current medical image obtained by imaging the same subject, the current image being obtained later than the previous medical image; a second measuring unit to measure a size of an abnormal shadow present on the other of the current medical image and the previous medical image, a position of the abnormal shadow on the other of the images corresponding to a position of the abnormal shadow on the one of the images; and a report outputting unit to generate a character string describing a change in the size of the abnormal shadow from the measured sizes of the two abnormal shadows and output a file of a report text about a case shown in the previous and current medical images, the report text containing the character string.

The program of the invention causing a computer to function as: a first measuring unit to measure a size of an abnormal shadow present on one of a previous medical image and a current medical image obtained by imaging the same subject, the current image being obtained later than the previous medical image; a second measuring unit to measure a size of an abnormal shadow present on the other of the current medical image and the previous medical image, a position of the abnormal shadow on the other of the images corresponding to a position of the abnormal shadow on the one of the images; and a report outputting unit to generate a character string describing a change in the size of the abnormal shadow from the measured sizes of the two abnormal shadows and output a file of a report text about a case shown in the previous and current medical images, the report text containing the character string.

The "abnormal shadow" herein means a shadow present in an image obtained by imaging an abnormal region, such as a tumor, and includes not only the shadow of the imaged abnormal region but also a shadow similar to the shadow of the imaged abnormal region.

The "size of the abnormal shadow" herein means an extent of the shape, area, volume, and/or the like, of the abnormal shadow. The "character string describing a change in the size of the abnormal shadow" herein means a string of characters that is arranged to describe the extent of the shape, area, volume, and/or the like, of the abnormal shadow.

The "report text about a case" herein means a text that describes a report about the case formed by a combination of character strings; however, the report text may contain a combination of character data and image data.

The apparatus of the invention may further include an inputting unit to input a position of the abnormal shadow on the one of the images, wherein the first measuring unit may measure the size of the abnormal shadow present at the inputted position.

In an aspect where the previous medical image and the current medical image include a plurality of slice images obtained by imaging the subject at predetermined slice intervals, the apparatus may further include an aligning unit to align slice positions of the slice images of the previous medical image and the current medical image to each other, and the first measuring unit and the second measuring unit may measure the size of the abnormal shadow from a corresponding pair of the slice images of the previous medical image and the current medical image aligned by the aligning unit.

The "corresponding pair of the slice images of the previous medical image and the current medical image" means the slice images of the previous medical image and the current medical image obtained by imaging substantially the same anatomic position of the subject, such as a human body.

According to the present invention, the sizes of the abnormal shadows present at corresponding positions on the previous medical image and the current medical image are automatically measured, and a character string describing a change in the size of the abnormal shadow is generated from the measured sizes of the two abnormal shadows, to output a file containing a report text. This allows generation of an image interpretation report describing the change of the abnormal shadow without requiring the diagnostician to carry out measurement every time.

In an aspect where the position of the abnormal shadow is inputted, an image interpretation report describing the change in the size of the abnormal shadow of interest can be generated only by specifying the abnormal shadow of interest.

Further, in an aspect where the previous medical image and the current medical image include a plurality of slice images obtained through imaging at certain slice intervals, slice positions of the slice images are automatically aligned so that an image interpretation report describing a change between abnormal shadows at corresponding positions can be generated.

BRIEF DESCRIPTION OF THE DRAWINGS

FIGS. 5A-5C show scores for respective regions for respective slices which are used in a region recognition process (5A shows region scores, 5B shows a weight map and 5C shows a cost map),
FIG. 8 is a block diagram illustrating the configuration of a report generating unit,
FIGS. 9A-9E are diagrams for explaining how an anatomic position is analyzed.

DESCRIPTION OF THE PREFERRED EMBODIMENTS

Figure 1:
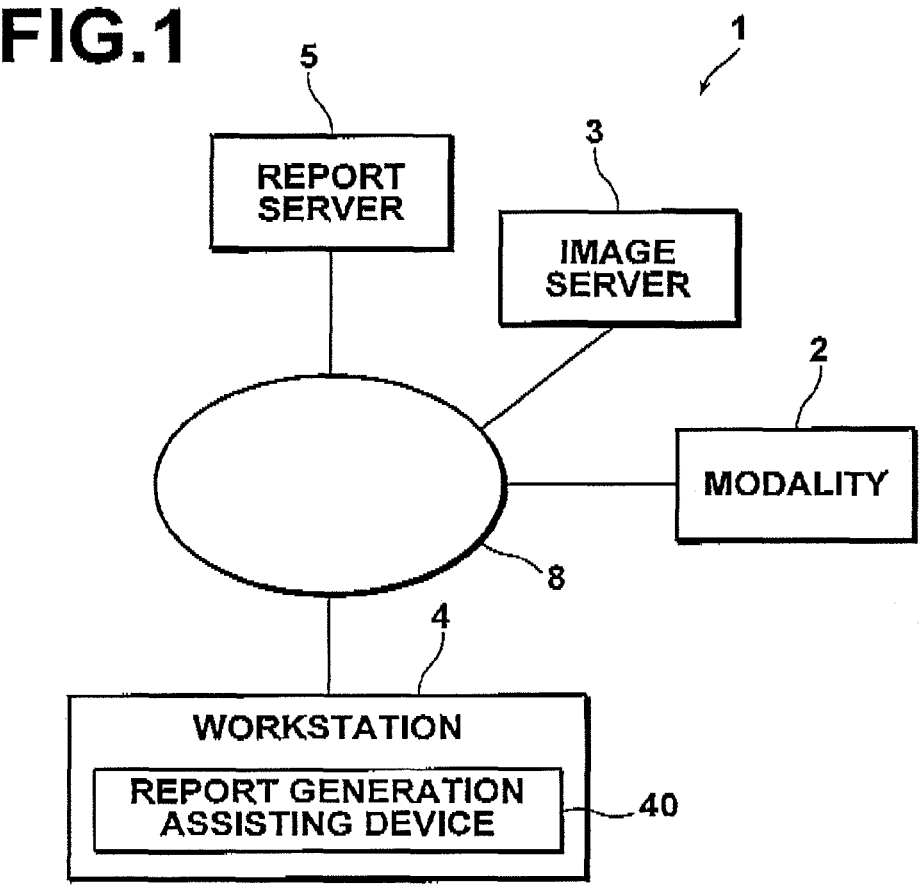
FIG. 1 is a block diagram illustrating the schematic configuration of a medical system.

Hereinafter, an embodiment of the present invention will be described with reference to the drawings. FIG. 1 is a block diagram showing the schematic configuration of a medical system incorporating a report generation assisting device according to the embodiment of the invention. As shown in FIG. 1, a medical system 1 of this embodiment includes a modality 2 to image a medical image, an image server 3 to store a medical image of an imaged lesion of a subject, a workstation 4 on which a diagnostician carries out image interpretation, a report server 5 to store a report generated by the diagnostician through image interpretation on the medical image displayed on the screen of the workstation 4, and a network 8.

The modality 2 is an apparatus or system, such as a CR (Computed Radiography), CT (Computed Tomography), MRI (Magnetic Resonance Imaging), PET (positron emission tomography) or US (Ultrasound imaging) apparatus or system, for recording a medical image of a patient as digital data.

The image server 3 stores a large number of medical images taken with each modality 2 installed at, for example, a department of radiology, which are received via the network 8, in a form complying with DICOM together with patient information of imaged subjects, imaging dates, modality information, and the like. The image server 3 has a database management software program installed thereon, and is provided with a function to search through the stored medical images using various types of information attached to the medical images.

The workstation 4 is provided with a function to retrieve a medical image to be interpreted from the medical images stored in the image server 3 via the network 8 and displays the medical image on the screen of the image display device. The workstation 4 is preferably provided with a high-definition display device, such as a high-definition CRT, for the image interpretation of the medical image by the person who interprets the image, such as a doctor.

The workstation 4 further has a report generation assisting program installed thereon, so that it can also function as a report generation assisting device 40.

The report server 5 stores a result of image interpretation of the medical image, which is carried out by the diagnostician on the workstation 4, as an image interpretation report. The stored image interpretation report is associated with the case image subjected to the image interpretation, which is stored in the image server 3.

The report generation assisting device 40 assists generation of image interpretation reports about various images, such as plain x-ray radiographic images taken with a CR apparatus, and slice images taken with a CT or MRI apparatus. In this embodiment, an explanation is given on a case where an image to be diagnosed (current medical image)

subjected to image interpretation is a slice image taken with a CR or MRI apparatus, and a report is generated about image interpretation of the slice image.

Figure 2:
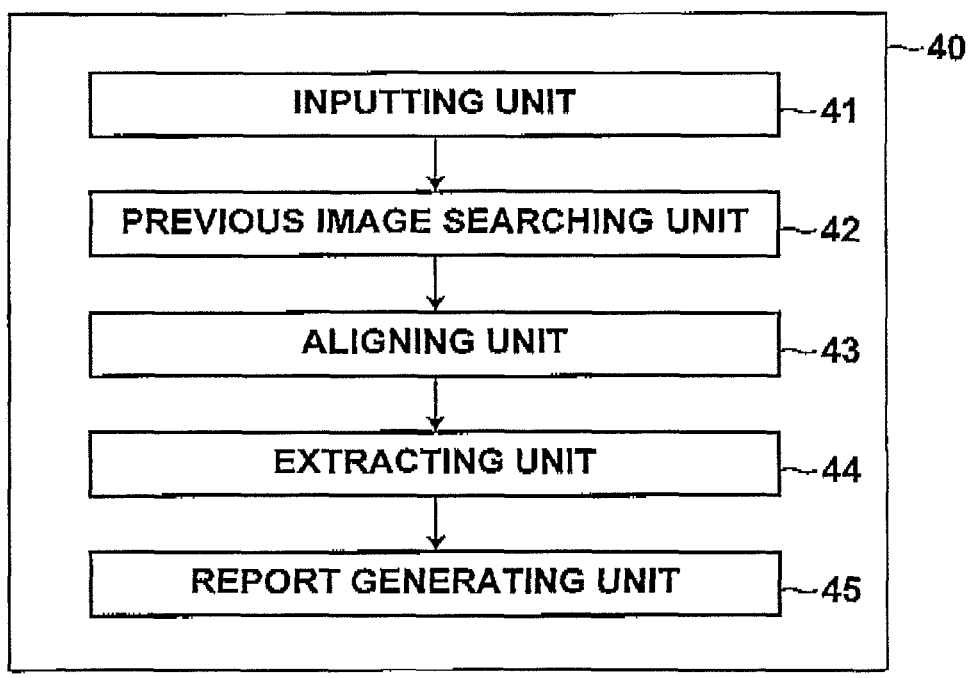
FIG. 2 is a block diagram illustrating the schematic configuration of a report generation assisting device.

As shown in FIG. 2, the report generation assisting device 40 includes an inputting unit 41 to input a position of an abnormal shadow on a current medical image, a previous image searching unit 42 to search out a previous medical image obtained by previously imaging the same region of the same subject as that captured in the current medical image, an aligning unit 43 to align the slice positions of the slice images of the previous and current medical images to each other, an extracting unit 44 to extract the abnormal shadow from the previous or current medical image, and a report generating unit 45 to generate a report about the current medical image. Hereinafter, in this embodiment, the current medical image is simply referred to as a current image and the previous medical image is simply referred to as a previous image.

The inputting unit 41 inputs the position, which is specified by means of an input device such as a mouse, of the abnormal shadow present on the current image displayed on the screen of the image display device. Specifically, for example, a point within a suspected abnormal shadow is specified by means of the input device such as a mouse, and the specified position is inputted as the position of the abnormal shadow.

The previous image searching unit 42 sends a search request for the previous image obtained by previously imaging the same region of the same subject as that captured in the current image to the image server 3, and receives the previous image from the image server 3.

The aligning unit 43 recognizes a head region, a head-neck region, a neck region, a chest region, a chest-abdominal region, an abdominal region, a pelvic region and a leg region based on a fact that these regions are captured in this order in the slice image taken with a CT or MRI apparatus.

Figure 3:
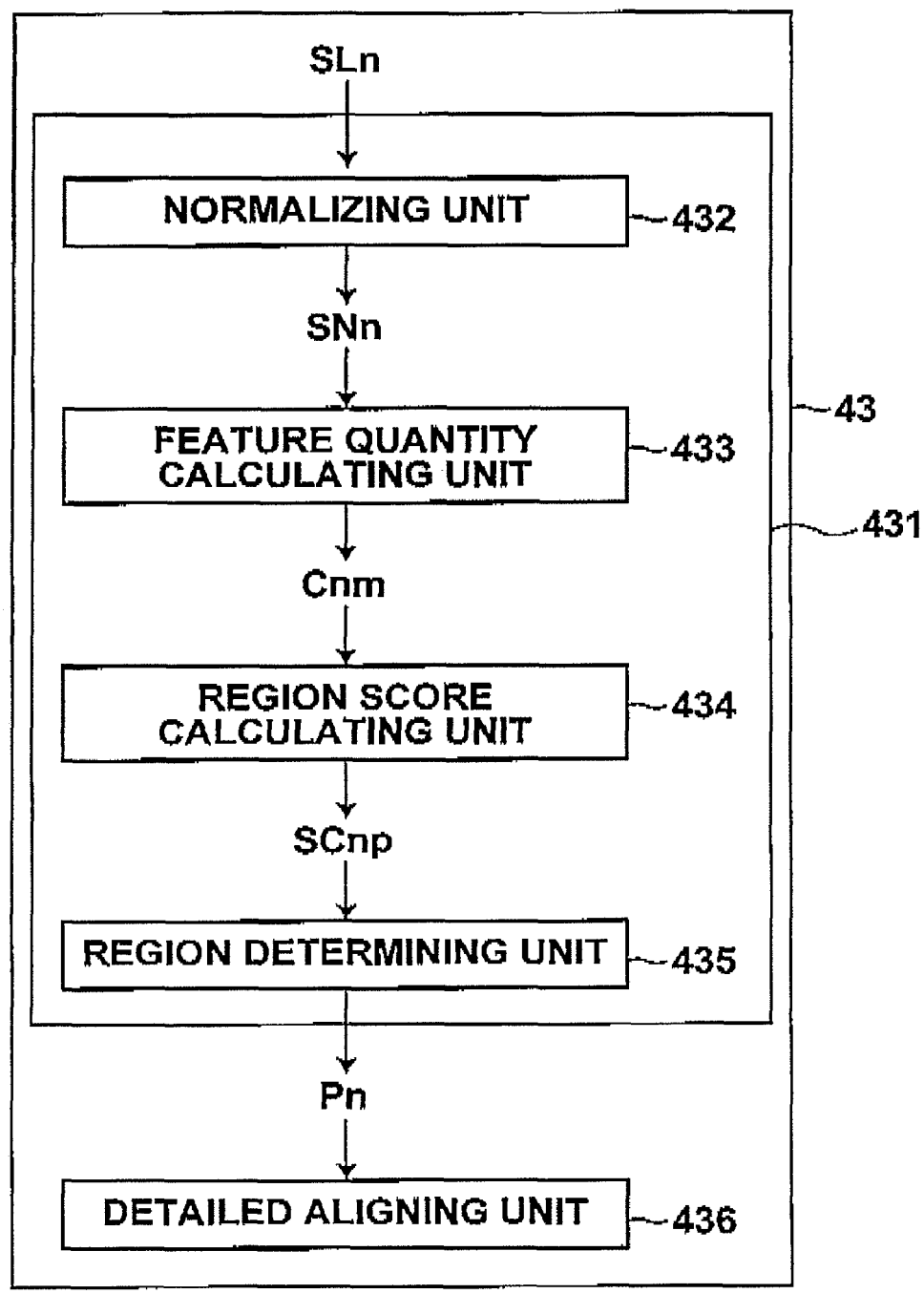
FIG. 3 is a block diagram illustrating the configuration of an aligning unit, FIGS. 4A-4D schematically illustrate how landmarks are set for normalization of a slice image.

As shown in FIG. 3, the aligning unit 43 includes a region recognition unit 431 and a detailed aligning unit 436. The region recognition unit 431 recognizes the respective regions, and the positions of the previous image and the current image along the body axis direction are roughly aligned to each other. Thereafter, the detailed aligning unit 436 aligns the slice positions of these slice images to each other in detail.

The region recognition unit 431 carries out a region recognition process on multiple CT slice images representing the body regions of a human body, which is the subject, determines the region represented by each slice image, and adds information indicating the determined region (such as a text representing the region name or a code identifying the region) to each corresponding slice image as attached information based on the DICOM standard, and outputs the information attached to the images. In the region recognition process, the regions represented in the slice images are determined such that the order of the body regions, i.e., the head region, the head-neck region, the neck region, the chest region, the chest-abdominal region, the abdominal region, the pelvic region and the leg region, is maintained when the slice images are arranged in the order from the top to the bottom of the human body.

As shown in FIG. 3, the region recognition unit 431 includes: a normalizing unit 432 to normalize inputted slice images $SL_n$ (n=1, 2, . . . ); a feature quantity calculating unit 433 to calculate a number of feature quantities $c_{nm}$ (m=1, 2, . . . ) of the normalized slice images $SN_n$; a region score calculating unit 434 to calculate a score for each region $sc_{np}$ (p=the head region, the head-neck region, the neck region, the chest region, the chest-abdominal region, the abdominal region, the pelvic region or the leg region) indicating the probability of each image representing each region by inputting the feature quantities $c_{nm}$ calculated for each normalized slice image $SN_n$ to classifiers, which have been obtained through AdaBoosting; and a region determining unit 435 to determine, from the calculated region scores $sc_{np}$ inputted thereto, a region $P_n$ shown in each inputted slice image $SL_n$ by using a dynamic programming technique, such that the order of the body regions is maintained.

The normalizing unit 432 extracts the human body region from each inputted image $SL_n$, calculates a landmark (reference point) from information of the extracted human body region, and applies affine transformation to the inputted image using the calculated landmark as a reference point to scale, translate and/or rotate the inputted image to generate the normalize image $SN_n$. The purpose of the normalization is to eliminate variations in the size or inclination of the human body regions in the inputted slice images $SL_n$ due to differences between individuals and/or imaging conditions and align positions of structures (such as bone regions and air regions) in the human body regions, thereby improving efficiency and accuracy of the subsequent region recognition process.

A technique used for extracting the human body region from each inputted image $SL_n$ may be any of methods known at the time of putting the present invention into practice. An example thereof is a technique in which the inputted image $SL_n$ is subjected to binarization and noise reduction, and then, contours of human body region candidates are extracted by contour extraction. Then, among the extracted contours, those having an area that is less than a predetermined threshold are removed, and a region within the remaining contour is determined as being the human body region (see Japanese Unexamined Patent Publication No. 9 (1997)-187444).

Figure 4A:
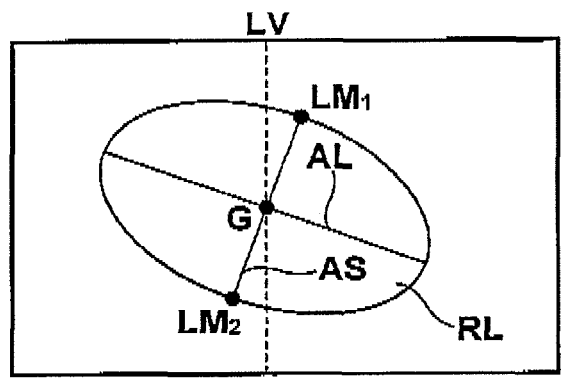
Figure 4B:
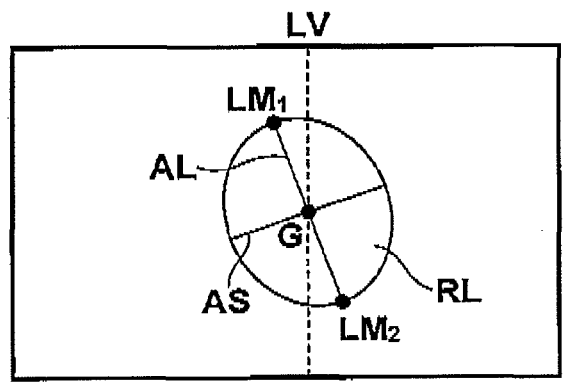
Figure 4C:
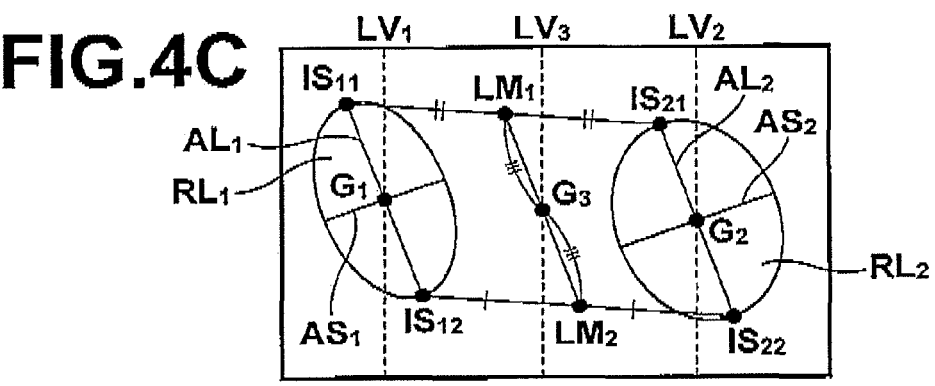
Figure 4D:
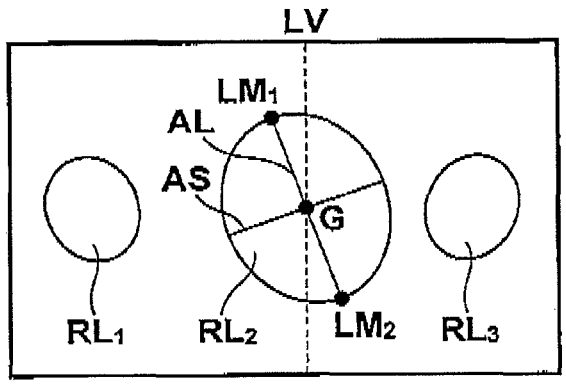

The landmark may, for example, be two points at which the contour line intersects with the median plane. Specifically, the landmarks can be found depending on the number of labels obtained through a labeling operation carried out on the extracted human body region, as shown in FIGS. 4A-4D. As shown in FIGS. 4A and 4B, if the number of labels is one, a centroid G of a labeled region (human body region) RL is found. Then, a major axis AL and a minor axis AS crossing the centroid G, and a straight line LV crossing the centroid G along the vertical direction of the slice image $SL_n$ are set. Then, points at which the contour line of the human body region RL intersects with one of the major axis AL and the minor axis AS forming a smaller angle with the straight line LV are set as landmarks $LM_1$ and $LM_2$. FIG. 4A schematically illustrates a case where the angle formed between the minor axis AS and the straight line LV is smaller than the angle formed between the major axis AL and the straight line LV, and this corresponds to an image representing the chest region, the chest-abdominal region, the abdominal region or the pelvic region. FIG. 4A schematically illustrates a case where the angle formed between the major axis AL and the straight line LV is smaller than the angle formed between the minor axis AS and the straight line LV, and this corresponds to an image representing the head region, the head-neck region or the neck region. FIG. 4C illustrates a case where the number of labels is two, and this corresponds to an image representing the leg region. In this case, centroids $G_1$, $G_2$ are found for labeled regions $RL_1$, $RL_2$, and major axes $AL_1$, $AL_2$ and minor axes $AS_1$, $AS_2$ crossing the centroids $G_1$, $G_2$, respectively, and straight lines $LV_1$, $LV_2$ crossing the centroids $G_1$, $G_2$ along the vertical direction of the slice image $SL_n$, respectively, are set. Then, for the respective labeled regions, intersecting points $IS_{11}$, $IS_{12}$, $IS_{21}$, $IS_{22}$ between the contour lines of the human body regions $RL_1$, $RL_2$ and ones of the major axes $AL_1$, $AL_2$ and the minor axes $AS_1$, $AS_2$ which form a smaller angle with the corresponding straight lines $LV_1$, $LV_2$ are found, and midpoints of line segments $IS_{11}$-$IS_{21}$ and $IS_{12}$-$IS_{22}$, which do not intersect with each other, are set as landmarks $LM_1$, $LM_2$. It should be noted that, if an area ratio of the two labeled regions is out of a predetermined range, i.e., if a difference between areas of the two labeled regions are larger than a predetermined threshold, then, one of the labeled regions having the smaller area is determined as being a medical tool, or the like, and the other of the labeled regions having the larger area is subjected to the same operation as that in the case where the number of labels is one. FIG. 4D illustrates a case where the number of labels is three, and this corresponds to an image representing the neck region and the arms. In this case, one of labeled regions $RL_1$, $RL_2$, $RL_3$ having the largest area ($RL_2$ in this case) is subjected to the same operation as that in the case where the number of labels is one to find the landmarks $LM_1$, $LM_2$. It should be noted that, in the cases shown in FIGS. 4A, 4B and 4D, if distances to the landmarks $LM_1$, $LM_2$ from the straight line LV are larger than a predetermined threshold, correction to shift the positions of the landmarks $LM_1$, $LM_2$ toward the straight line LV along the contour of the labeled region RL may be carried out. Similarly, in the case shown in FIG. 4C, if distances to the landmarks $LM_1$, $LM_2$ from the straight line $LV_3$, which crosses the midpoint $G_3$ of the line segment $LM_1$-$LM_2$ along the vertical direction of the slice image $SL_n$, is larger than a predetermined threshold, correction to shift the positions of the landmarks $LM_1$, $LM_2$ toward the straight line $LV_3$ along the line segments $IS_{11}$-$IS_{21}$ and $IS_{12}$-$IS_{22}$ may be carried out. A specific example of a shift amount may be such that the distances from the landmarks $LM_1$, $LM_2$ to the straight line LV or $LV_3$ is reduced by 20%.

The thus found landmarks $LM_1$, $LM_2$ are used as references to normalize each slice image $SL_n$ through affine transformation, and the like, such that the two landmarks $LM_1$, $LM_2$ are positioned at the center in the horizontal direction of the slice image $SL_n$ and a distance between the two landmarks has a predetermined value.

The feature quantity calculating unit 433 calculates the multiple types of feature quantities $c_{nm}$ for each of the normalize images $SN_n$. Specific examples of the feature quantities $c_{nm}$ may include pixel values within a block (3×3 pixels, for example) set in the normalized image $SN_n$, an average, a maximum value, a minimum value and a median of the pixel values, a ratio of air regions or bone regions, which are extracted thorough thresholding based on CT values, in the human body region to the human body region, and a ratio of an area of the human body region to an area of a circle having the same perimeter (circumference) as the perimeter of the human body region (a degree of circularity). The feature quantities $c_{nm}$ may be represented by calculated values without any conversion or by quantized values of the calculated values.

The region score calculating unit 434 calculates for each slice image $SL_n$ a region score $sc_{np}$, which indicates a probability of the slice image representing each region, by inputting the feature quantities $c_{nm}$ to a classifier group for each region, which is obtained through a learning process based on AdaBoosting. The classifier group for each region is obtained through a learning process based on AdaBoosting by using the multiple types of feature quantities which are calculated in the same manner as described above for each of images serving as learning samples that include images which are known in advance to represent the region of interest and images which are known in advance not to represent the region of interest. The classifier group for determining a single region contains one or more classifiers. If the classifier group contains two or more classifiers, the classifiers have a mutually complementary relationship between their classifying abilities. The number of classifier groups to be generated is the same as the number of regions to be determined, and the types of the feature quantities are determined for each classifier group. Details of the learning process and the calculation of the region score are disclosed in Japanese Unexamined Patent Publication No. 2005-108195, for example. In addition to the above-mentioned method, the calculation of the region score may also be achieved by a method using classifiers which are generated through any of other learning processes such as artificial neural network (ANN), support vector machine (SVM) or relevance vector machine (RVM), or by a method using a lookup table for determining a region score for a single feature quantity or a combination of more than one feature quantities. Further, the operations carried out by the feature quantity calculating unit 433 and the region score calculating unit 434 may be replaced with template matching for each region disclosed in Japanese Unexamined Patent Publication No. 2005-160502 or a method disclosed in Japanese Unexamined Patent Publication No. 2006-155002 in which a degree of similarity obtained through comparison with a unique image for each region is used as the region score.

Through the above-described operation, the score $sc_{np}$ for each region is calculated for each slice image $SL_n$. FIG. 5A shows a table containing one example of scores $sc_{np}$ for the respective regions calculated for the respective slice images (slices) $SL_n$, where the larger the value of the region score $sc_{np}$, the higher the probability of the slice image representing the corresponding region. Following the regions having the largest region scores $sc_{np}$ for the respective slices $SL_n$ in this table, i.e., the head-neck region for the slice 1, the head-neck region for the slice 2, the neck region for the slice 3, the chest region for the slice 4, the neck region for the slice 5 and the chest region for the slice 6, there is an unconformity with the order of the human body regions between the slice 4 and the slice 6. Therefore, the region determining unit 435 carries out the following correction.

The region determining unit 435 makes final determination on the regions $P_n$ shown in the respective slice images $SL_n$ so that no unconformity is introduced between the order of the largest values of the region scores $sc_{np}$ of the respective slice images $SL_n$ and the order of the body regions of the human body, namely, reference regions arranged in the order of the head region, the head-neck region, the neck region, the chest region, the chest-abdominal region, the abdominal region, the pelvic region and the leg region, which is generated in advance. In this case, the final determination of the regions $P_n$ is made by finding a shortest path with a smallest cost, where a cost is imposed if there is an unconformity between the reference regions and the largest values of the region scores $sc_{np}$ of the respective slice images $SL_n$. Specifically, a technique for solving an optimization problem can be used, and in this embodiment, a technique using dynamic programming (DP matching) is explained as a specific example thereof.

First, for the region scores $sc_{np}$ shown in FIG. 5A, each score value is subtracted from the largest value of the region scores $sc_{np}$ for each slice. Through this operation, a weight map is generated, as shown in FIG. 5B, where the magnitude correlation between the region scores $sc_{np}$ is inverted, that is, values of the region scores $sc_{np}$ are converted into values of zero or more, and the score value of the region having the highest region score $sc_{np}$ is converted into zero. It should be noted that the conversion for generating the weight map may be achieved by means of a lookup table in stead of the above-described subtraction.

Then, the path with the smallest cost is calculated through DP matching from the inputted weight map shown in FIG. 5B. Here, a description of a technique proposed in Japanese Patent Application No. 2006-140041 by the applicant of the present application is cited. First, a cost map as shown in FIG. 5C is generated from the inputted weight map of FIG. 5B. In FIG. 5C, a cost for each cell (n,p) is set as follows, where n represents a slice number and p represents a region number (1: head-neck region, 2: neck region, 3: chest region).

(1,1): a value at (1,1) in the weight map (see FIG. 5B), (n, 1): a value at (n−1, 1) in the weight map+a predetermined value (0 in this example), (1,m): a value at (1,m−1) in the weight map+a predetermined value (0 in this example), (n,m): the smallest value among (i)-(iii) below;

(i) a value at (n−1,m−1) in the cost map+a value at (n,m) in the weight map, (ii) a value at (n,m−1) in the cost map+a value at (n,m) in the weight map+a predetermined value (1.0 in this example), and (iii) a value at (n−1,m) in the cost map+a value at (n,m) in the weight map+(1.0 in this example).

Then, neighboring smallest values are sequentially followed from the right to the left in the cost map. Thus, a map representing a correspondence between the slice numbers and the regions is generated.

Figure 6:
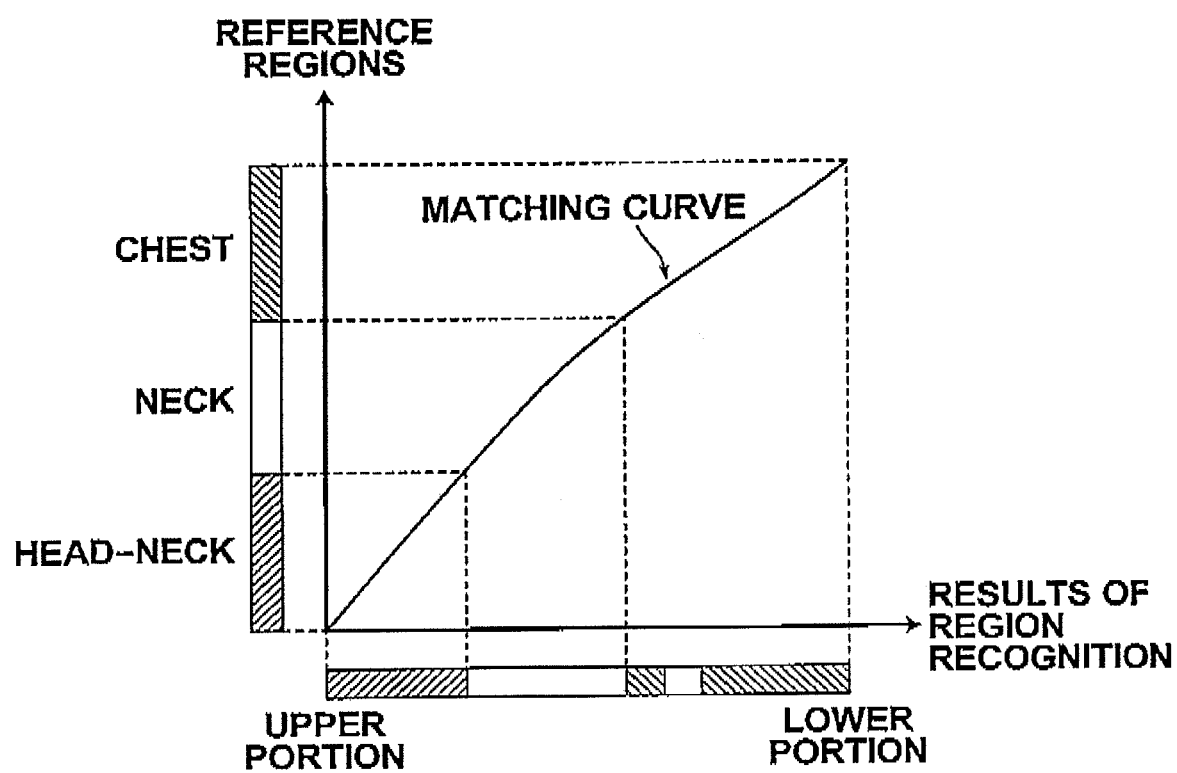
FIG. 6 shows one example of a matching curve which is used in the region recognition process.

Then, temporary recognition results are replaced with corresponding reference regions based on a matching curve shown in FIG. 6, which plots the order of the body regions of the human body (the reference regions) along the longitudinal axis and the temporary recognition results based on the largest values of the region scores $sc_{np}$ of the slices $SL_n$ along the transverse axis, to achieve the operation for finally determining the regions in the slices $SL_n$.

The detailed aligning unit 436 aligns the slice positions of the slice images to each other according to the rough region recognition carried out by the region recognition unit 431. For example, if the region recognition unit 431 has recognized that slice numbers 1-100 of the current image represent the chest region and slice numbers 101-150 of the current image represent the abdominal region, and slice numbers 1-120 of the previous image represent the chest region and slice numbers 121-180 of the previous image represent the abdominal region, it is determined that the slice numbers 1-100 of the current image and the slice numbers 1-120 of the previous image correspond to each other. Further, detailed alignment between the slices of the current image and the slices of the previous image is carried out using a technique such as one disclosed in William F. Sensakovic et al., "Automated matching of temporally sequential CT sections", Med. Phys., Vol. 31, No. 12, pp. 3417-3424, 2004, to achieve the alignment between the slice positions such that, among the slice numbers 1-100 of the current image and the slice numbers 1-120 of the previous image, the slice number 10 of the current image corresponds to the slice number 20 of the previous image.

The extracting unit 44 searches around the specified or set point on the image from which the abnormal shadow is to be detected, and extracts the abnormal shadow, such as a tumor region. The specified or set point is preferably near the center of the tumor region.

Figure 7:
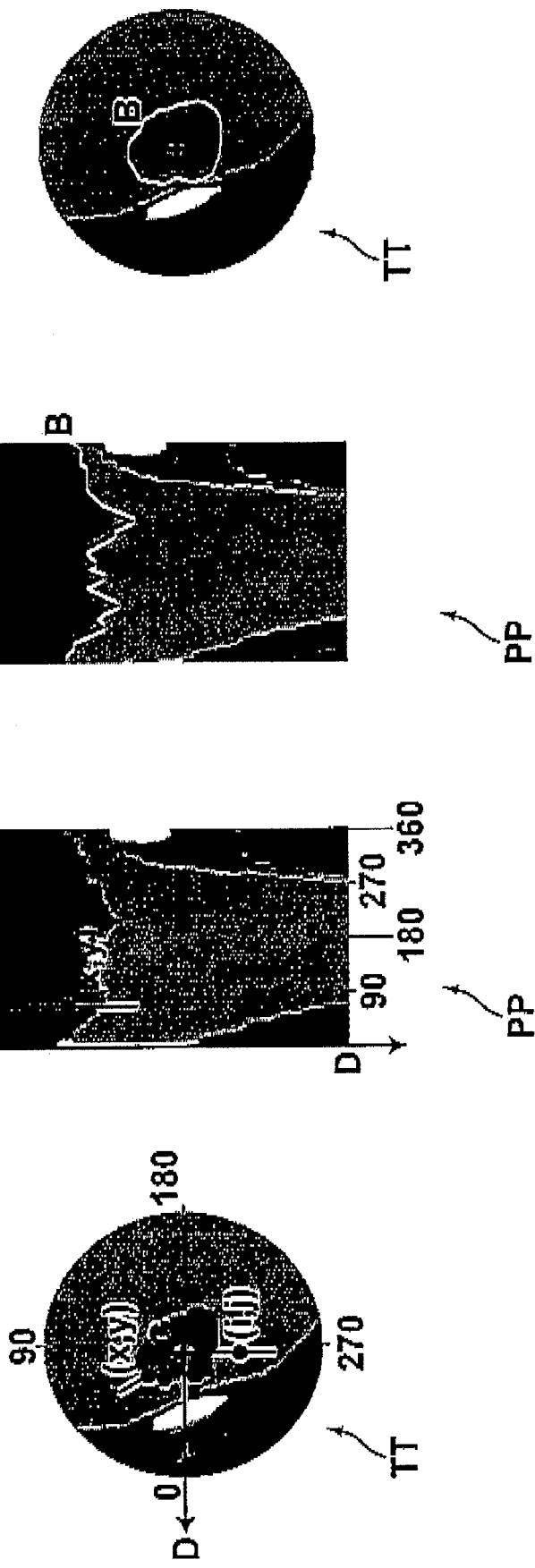
FIGS. 7A-7D are diagrams for explaining how an abnormal shadow
    automatically extracted.

First, as shown in FIG. 7A, an area having a certain radius, which is large enough for containing the tumor region, around the specified or set point C is determined as a discrimination area TT. Then, the image of the discrimination area TT, such as one shown in FIG. 7A, is transformed into a discrimination image PP in a polar coordinate plane, which is represented by distances from the center point C and angles θ formed with a straight line crossing the center point C. For example, using the image in the polar coordinates shown in FIG. 7B, which is obtained through the polar coordinate transformation with defining the angle θ in the clockwise direction from a line segment CD extending in the radial direction of the image shown in FIG. 7A, determination is made as to whether each pixel in the discrimination area represents the contour of the tumor region.

For each pixel (x,y) in the discrimination area, an assessment value S, which indicates whether or not the pixel represents the contour, is calculated based on a feature quantity L, which is extracted from luminance information of one-dimensional luminance profile along a straight line crossing the pixel (x,y) in the discrimination area and the point C.

In the one-dimensional luminance profile along the straight line crossing each pixel (x,y) and the point C, there are sudden changes in the luminance value in the vicinity of the contour of the tumor region. Therefore, the feature quantities are calculated from the luminance values, and classifiers are generated using these feature quantities. Based on results obtained from the classifiers, an image (x,y) forming a contour, such as one represented by the bold line B shown in FIG. 7C, is found. Then, inverse coordinate transformation is applied to the discrimination area TT in the polar coordinates to transform the image into the ordinary coordinates and the contour on the image of the discrimination area TT is determined as shown FIG. 7D. The region surrounded by the contour is extracted as the tumor region (i.e., the abnormal shadow).

Alternatively, the abnormal shadow may be extracted using a region separation technique such as one shown in Wormanns D. et al., "Volumetric measurements of pulmonary nodules at multi-row detector CT: in vivo reproducibility", Eur Radiol, Vol. 14, No. 1, 2004.

The report generating unit 45 includes: a first measuring unit 451 to measure the size of the abnormal shadow present on the current medical image; a second measuring unit 452 to measure the size of the abnormal shadow present at a position on the previous medical image that corresponds to the position of the abnormal shadow present on the current medical image; a position analyzing unit 453 to analyze an anatomic position of the abnormal shadow on the current image; and a report outputting unit 454 to output a file of a report text about the case shown in the previous and current medical images.

The first and second measuring units 451 and 452 measure the size of the abnormal shadow that is extracted by the extracting unit 44. The size of the abnormal shadow is indicated, for example, by an area, a volume, a major axis and a minor axis, and these values are automatically measured.

The position analyzing unit 453 analyzes the anatomic position of the abnormal shadow extracted by the extracting unit 44. For example, in a case of a chest region image, as shown in FIG. 9, first, the lung fields (see at "b" in FIG. 9) and the bronchial tubes (see at "d" in FIG. 9) are automatically extracted from an inputted chest region image (see at "a" in FIG. 9). Further, the interlobar fissures are extracted (see at "c" and "e" in FIG. 9) based on the shape of the bronchial tubes to classify the lung lobes of each lung field (right superior, middle and inferior lobes, left superior and inferior lobes) (for details, see, for example, ref. 1: T. Hayashi et al., "Development of the Procedure for Automatic Extracting Interlobar Fissures and its Performance Evaluation", Thecnical Report of IEICE, MI2003-53, pp. 39-44, 2003, ref. 2: "Nakata et al., "Consideration on classification of lobes of bronchial tubes extracted from three-dimensional chest region CT images", 15th CADM, pp. 275-276, 2005, ref. 3:

"Tanaka et al., "Automatic classification of arteria pulmonalis and vena pulmonalis from X-ray CT chest images based on spatial position characteristics of blood vessels and bronchial tubes", Journal of the Institute of Electronics, Information and Communication Engineers, DII, Vol. J88, pp. 1421-1431, 2005, and ref. 4; "Shyu C et al., "a physician-in-the-loop content-based image retrieval system for HRCT image databases", Computer Vision and Image Understanding, pp. 111-132, 1999). For example, the anatomic position of the abnormal shadow (indicated by the black arrow) shown at "a" in FIG. 9 is recognized as "left lung, superior lobe, S2".

Figures 10, 11, 12:
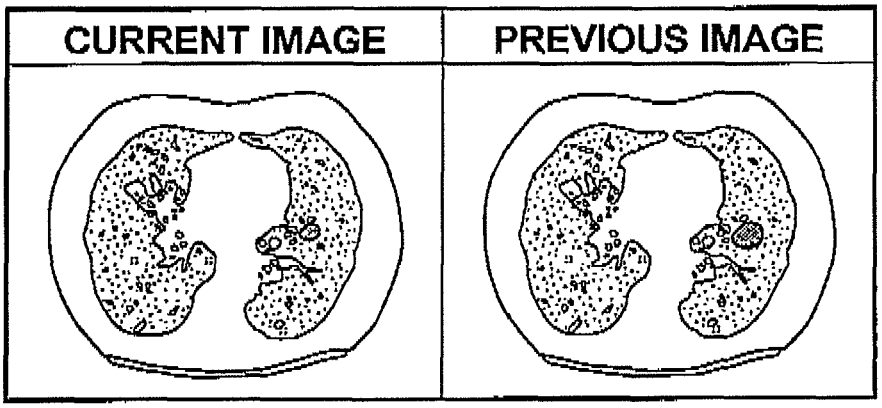
FIG. 10 shows a display example of current and previous images.
FIG. 11 shows one example of a report text generated with character strings (a first example)
FIG. 12 shows one example of a report text generated with character strings (a second example)

The report outputting unit 454 outputs a file containing, in a report text about the case shown in the previous and current medical images, character strings that describe a change in the measured size of the two abnormal shadows and character strings that describe the anatomic position of the abnormal shadow (see FIGS. 11 and 12).

Figure 13:
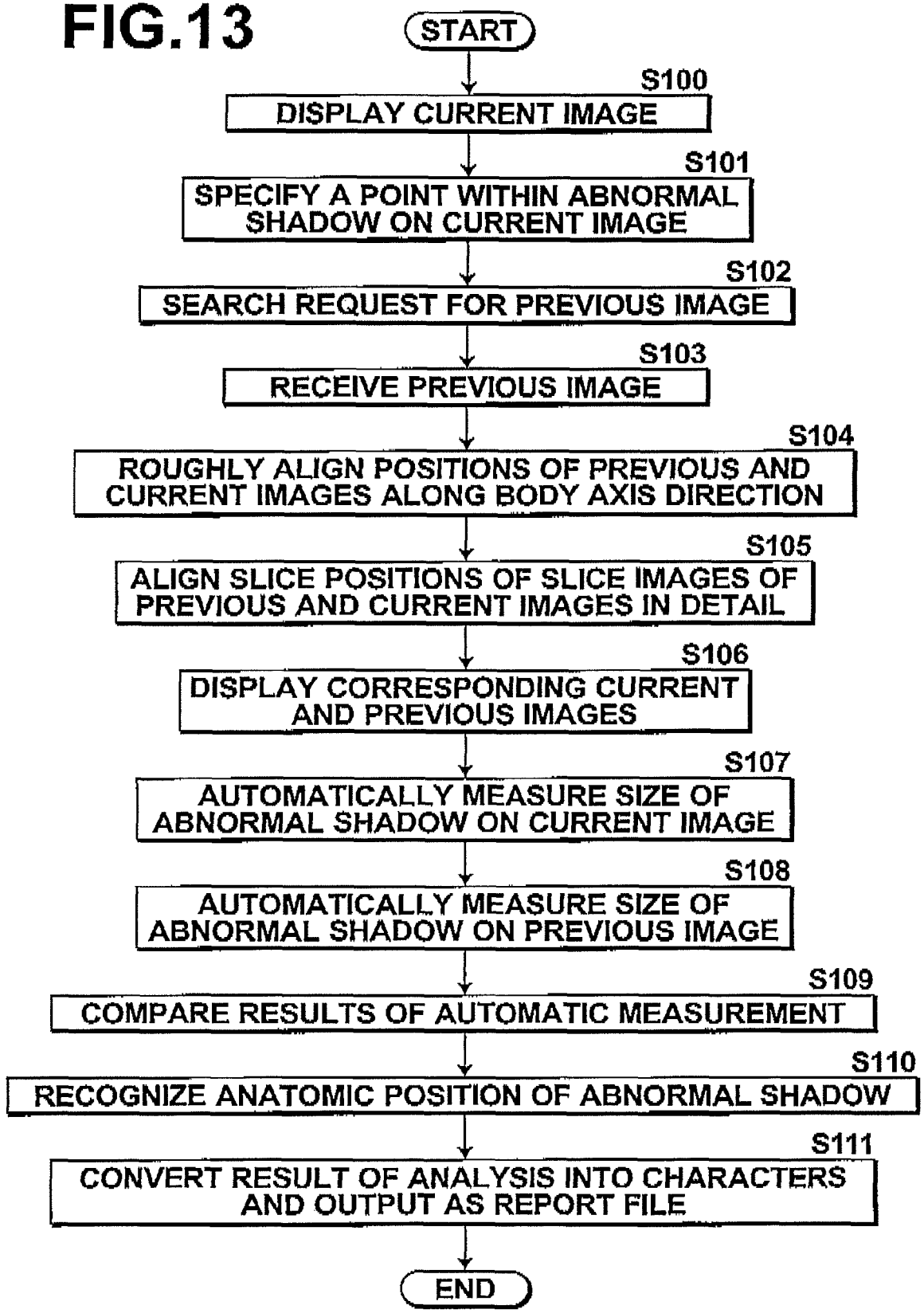
FIG. 13 is a flow chart showing the flow of a process to generate a follow-up observation report about the previous and current images.

Now, the flow of a process to generate a follow-up observation report about the previous and current images using the report generation assisting device of the invention will be described based on a flow chart shown in FIG. 13.

First, the diagnostician retrieves the current image obtained by imaging a subject to be diagnosed from the image server 3 and displays the image on the display device of the workstation 4 (S100). Slice images of the displayed current image are displayed in turn, and if a shadow which is suspected to be an abnormal shadow is found, a point near the center of the abnormal shadow present on the slice image is specified by clicking the point by means of the pointing device, such as a mouse (S101). In order to diagnose the stage of progress of the lesion in comparison with the previous condition of the specified abnormal shadow, first, the previous image searching unit 42 of the report generation assisting device 40 sends a search request to the image server 3 for the previous image that was previously obtained by imaging the same region of the same subject with the same modality 2 as those of the current image (S102), and receives the previous image from the image server 3 (S103).

In order to compare the currently observed slice image with the other slice image of the same slice position, the slice images of the received previous image and the current image are aligned to each other. First, the region recognition unit 431 roughly recognizes the regions along the body axis direction in the previous and current images and roughly aligns the positions along the body axis direction of the previous and current images (S504). Then, the detailed aligning unit 436 aligns the slice positions of the slice images in detail to each other (S105). Based on the aligned slice positions, one of the slice images of the previous image that corresponds to the displayed slice image of the current image is displayed side by side with the current image, as shown in FIG. 10 (S106).

At the first measuring unit 451, using the point clicked on the slice image of the current image as a reference, the extracting unit 44 searches around the specified point and extracts the abnormal shadow from the current slice image. Further, the size of the extracted abnormal shadow is automatically measured (S107). For example, in the current image shown in FIG. 10:
the area "Area"=55.2 mm$^2$,
the major axis "Axis major"=9.5 mm, and the minor axis "Axis minor"=6.8 mm.

Further, At the second measuring unit 452, the regions of the lung fields in the current and previous slice images are aligned and a point that corresponds to the specified point on the current slice image is set on the previous slice image. Then, the extracting unit 44 searches around the set point and extracts the abnormal shadow from the previous slice image, and the size of the extracted abnormal shadow is automatically measured (S108). For example, in the previous image shown in FIG. 10;
the area "Area"=70.119 mm$^2$
the major axis "Axis major"=10.8 mm, and the minor axis "Axis minor"=6.8 mm.

Comparing the results of automatic measurement of the current and previous images obtained by the first and second measuring units 451 and 452:
a major axis ratio: 0.78%, and
an area ratio: 0.87%
are obtained (S109).

The report outputting unit 454 carries out diagnosis based on the results of the automatic measurement of the current and previous images obtained by the first and second measuring units 451 and 452, and carries out classification depending on whether the abnormal shadow present on the previous image has disappeared, reduced or increased on the current image, as follows:
CR (Complete Response): the tumor has disappeared,
PR (Partial Response): the tumor has reduced by a rate of 50% or more,
NC (No Change): the tumor has reduced by a rate of less than 50% or increased by a rate of less than 25%, and
PD (Progressive Disease): the tumor has increased by a rate of 25% or more.

Further, the position analyzing unit 453 analyzes the anatomic position of the abnormal shadow extracted by the extracting unit 44, and the anatomic position is recognized as "left lung, superior lobe, S2" (S110). The report outputting unit 454 converts these results of the analysis into character strings, and outputs a file of a report text containing the character strings describing the change in the size of abnormal shadow and the character strings describing the anatomic position of the abnormal shadow, as shown in FIG. 11 (S111). This file is stored in the report server 5 as an image interpretation report.

Alternatively, these character strings may be inserted in a report text form, which has been prepared in advance, to form an output as shown in FIG. 12. FIG. 12 illustrates an example of a template, in which the character strings can be inserted at portions between "<" and ">".

As described in detail above, the user can simply specify a point on the current image to automatically search a corresponding previous image and automatically generate a follow-up observation report about the previous and current images. Further, by automatically calculating a change in the size, or the like, measurement can always be carried out with a constant accuracy.

Although, in the above-described embodiment, the size of the abnormal shadow on the current medical image is measured first, and then the size of abnormal shadow present on the corresponding position on the previous medical image is measured, the size of the abnormal shadow in the previous medical image may be measured first, and then the size of the abnormal shadow present on the corresponding position on the current medical image may be measured.

The above description is given on the case of slice images. However, even if there is only a single image such as in a case of a plain x-ray radiographic image, the position of an organ such as lung fields can automatically be aligned and a report can automatically be generated.

Further, if more than one nodules are present, the respective nodules may be clicked and the comparison may be made using a sum of the areas to indicate a change in the size of abnormal shadow.

Furthermore, if only one abnormal shadow is present, the position of the abnormal shadow may not be specified, and the abnormal shadow may be detected using a CAD function, to automatically generate a report about the size of the detected abnormal shadow.

What is claimed is:

1. An apparatus for assisting report generation, the apparatus comprising:
   a first measuring unit to measure a size of an abnormal shadow present on one of a previous medical image and a current medical image obtained by imaging the same subject, the current image being obtained later than the previous medical image;
   a second measuring unit to measure a size of an abnormal shadow present on the other of the current medical image and the previous medical image, a position of the abnormal shadow on the other of the images corresponding to a position of the abnormal shadow on the one of the images;
   a report outputting unit to automatically generate a character string describing a change in the size of the abnormal shadow based on the results of measurement by the first measuring unit and the results of measurement by the second measuring unit and output a file of a report text about a case shown in the previous and current medical images, the report text containing the character string;
   a detailed positional aligning unit for positionally aligning the previous medical image and the current medical image; and
   an extracting unit for extracting abnormal shadows from within a region in a periphery of a set point;
   the first measuring unit employing the extracting unit to extract and measure sizes of abnormal shadows which are present in the periphery of the set point within the one of the previous medical image and the current medical image; and
   the second measuring unit determining the position of a set point within the other of the images corresponding to the set point in the one of the images based on positional alignment data obtained by the detailed positional aligning unit, and employing the extracting unit to extract and measure sizes of abnormal shadows which are present in the periphery of the corresponding set point within the other of the image.

2. The apparatus for assisting report generation as claimed in claim 1, further comprising an inputting unit to input a position of the abnormal shadow on the one of the images,
   wherein the first measuring unit measures the size of the abnormal shadow present at the inputted position,
   wherein the inputted position is that of the set point within the one of the images.

3. The apparatus for assisting report generation as claimed in claim 1, wherein
   the previous medical image and the current medical image comprise a plurality of slice images obtained by imaging the subject at predetermined slice intervals,
   the apparatus further comprising an aligning unit to align slice positions of the slice images of the previous medical image and the current medical image to each other, and
   the first measuring unit and the second measuring unit measure the size of the abnormal shadow from a corresponding pair of the slice images of the previous medical image and the current medical image aligned by the aligning unit.

4. The apparatus for assisting report generation as claimed in claim 2, wherein
   the previous medical image and the current medical image comprises a plurality of slice images obtained by imaging the subject at predetermined slice intervals,
   the apparatus further comprising an aligning unit to align slice positions of the slice images of the previous medical image and the current medical image to each other, and
   the first measuring unit and the second measuring unit measure the size of the abnormal shadow from a corresponding pair of the slice images of the previous medical image and the current medical image aligned by the aligning unit.

5. A non-transitory computer readable medium embodied with a program for causing a computer to function as:
   a first measuring unit to measure a size of an abnormal shadow present on one of a previous medical image and a current medical image obtained by imaging the same subject, the current image being obtained later than the previous medical image;
   a second measuring unit to measure a size of an abnormal shadow present on the other of the current medical image and the previous medical image, a position of the abnormal shadow on the other of the images corresponding to a position of the abnormal shadow on the one of the images; and
   a report outputting unit to automatically generate a character string describing a change in the size of the abnormal shadow based on the results of measurement by the first measuring unit and the results of measurement by the second measuring unit and output a file of a report text about a case shown in the previous and current medical images, the report text containing the character string;
   a detailed positional aligning unit for positionally aligning the previous medical image and the current medical image; and
   an extracting unit for extracting abnormal shadows from within a region in a periphery of a set point;
   the first measuring unit employing the extracting unit to extract and measure sizes of abnormal shadows which are present in the periphery of the set point within the one of the previous medical image and the current medical image; and
   the second measuring unit determining the position of a set point within the other of the images corresponding to the set point in the one of the images based on positional alignment data obtained by the detailed positional aligning unit, and employing the extracting unit to extract and measure sizes of abnormal shadows which are present in the periphery of the corresponding set point within the other of the images.

* * * * *